(12) United States Patent
Hong et al.

(10) Patent No.: US 7,955,562 B2
(45) Date of Patent: Jun. 7, 2011

(54) CHEMICAL SENSOR USING THIN-FILM SENSING MEMBER

(75) Inventors: Ki-ha Hong, Seoul (KR); Hyuk-soon Choi, Seongnam-si (KR); Jong-seob Kim, Suwon-si (KR); Jai-kwang Shin, Anyang-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 106 days.

(21) Appl. No.: 12/385,284

(22) Filed: Apr. 3, 2009

(65) Prior Publication Data

US 2010/0079130 A1 Apr. 1, 2010

(30) Foreign Application Priority Data

Sep. 26, 2008 (KR) .................. 10-2008-0094741

(51) Int. Cl.
*G01N 27/04* (2006.01)
*G01N 30/62* (2006.01)

(52) U.S. Cl. .............................. 422/98; 422/88; 977/957
(58) Field of Classification Search .................. 422/50, 422/83, 88, 98; 977/902, 932, 953, 957
See application file for complete search history.

(56) References Cited

U.S. PATENT DOCUMENTS

2006/0214156 A1* 9/2006 Pan et al. .................. 257/40
2008/0094051 A1 4/2008 Williams et al.

* cited by examiner

*Primary Examiner* — Glenn Caldarola
*Assistant Examiner* — Randy Boyer
(74) *Attorney, Agent, or Firm* — Harness, Dickey & Pierce, P.L.C.

(57) ABSTRACT

Provided is a chemical sensor that may include a first electrode on a substrate, a sensing member covering the first electrode on the substrate, and a plurality of second electrodes on a surface of the sensing member exposing the surface of the sensing member. The chemical sensor may be configured to measure the change in electrical characteristics when a compound to be sensed is adsorbed on the sensing member. Provided also is a chemical sensor array including an array of chemical sensors.

10 Claims, 6 Drawing Sheets

CHEMICAL SENSOR USING THIN-FILM SENSING MEMBER

CROSS-REFERENCE TO RELATED APPLICATION

This application claims priority under 35 U.S.C. §119 to Korean Patent Application No. 10-2008-0094741, filed on Sep. 26, 2008, in the Korean Intellectual Property Office (KIPO), the entire contents of which are incorporated herein by reference.

BACKGROUND

1. Field

Example embodiments relate to a chemical sensor including a sensing member having a relatively large area and a nano structure, for example, a nanowire, for use in an upper electrode.

2. Description of the Related Art

Studies have been conducted on the diagnosis of disease by measuring the components of a chemical compound in the breath of people. For example, in the case of lung cancer patients and breast cancer patients, approximately 10 kinds of volatile organic compounds are discharged in the breath, unlike in a healthy person. Thus, a chemical sensor analyzing the components of the volatile organic compounds may be used for detecting diseases. A conventional chemical sensor may measure an amount of a chemical compound using a characteristic of a compound molecule in which the electrical conductivity or specific electrical resistance of the compound molecule changes according to the adsorption of the chemical compound.

Volatile organic compounds (VOCs) may be relatively stable, and thus, analyzing their components using an electrical method may be difficult. Gas chromatography (GC) may be used to analyze the VOCs; however, the sensor may be relatively large and expensive.

Sensors using semiconductors offer some advantages. For example, sensors using semiconductors may be relatively inexpensive and the detection may be performed in real-time. Additionally, sensors using semiconductors may be relatively small. However, detection sensitivity associated with the sensors using semiconductors may be relatively low and detecting stable materials, e.g. the VOCs, may be difficult.

A VOC measuring sensor using a conductive polymer has been proposed. When the conductive polymer adsorbs a VOC, the work function of the conductive polymer changes due to various reasons, for example, the swelling of the conductive polymer, and thus, a VOC may be detected by measuring the changes of the work function of the conductive polymer. However, sensors using a conductive polymer still have difficulty in reaching a detection capability of a few ppm. The difficulty is due to the volume of a sensing channel being too large to detect a small amount of electrical change according to adsorbed material.

SUMMARY

Example embodiments include a chemical sensor that has increased detection sensitivity by using a thin-film sensing member having a large sensing area. Example embodiments also disclose a chemical sensor array.

In accordance with example embodiments, a chemical sensor may include a first electrode on a substrate, a sensing member covering the first electrode on the substrate, and a plurality of second electrodes on a surface of the sensing member exposing the surface of the sensing member. In accordance with example embodiments, the chemical sensor may be configured to measure the change of electrical characteristics generated when a compound to be sensed is adsorbed on the sensing member.

In accordance with example embodiments, a chemical sensor array may include a plurality of the above described chemical sensors arranged in an array on a substrate. In accordance with example embodiments, the sensing members of the chemical sensors may be configured to detect compounds that are different from each other.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
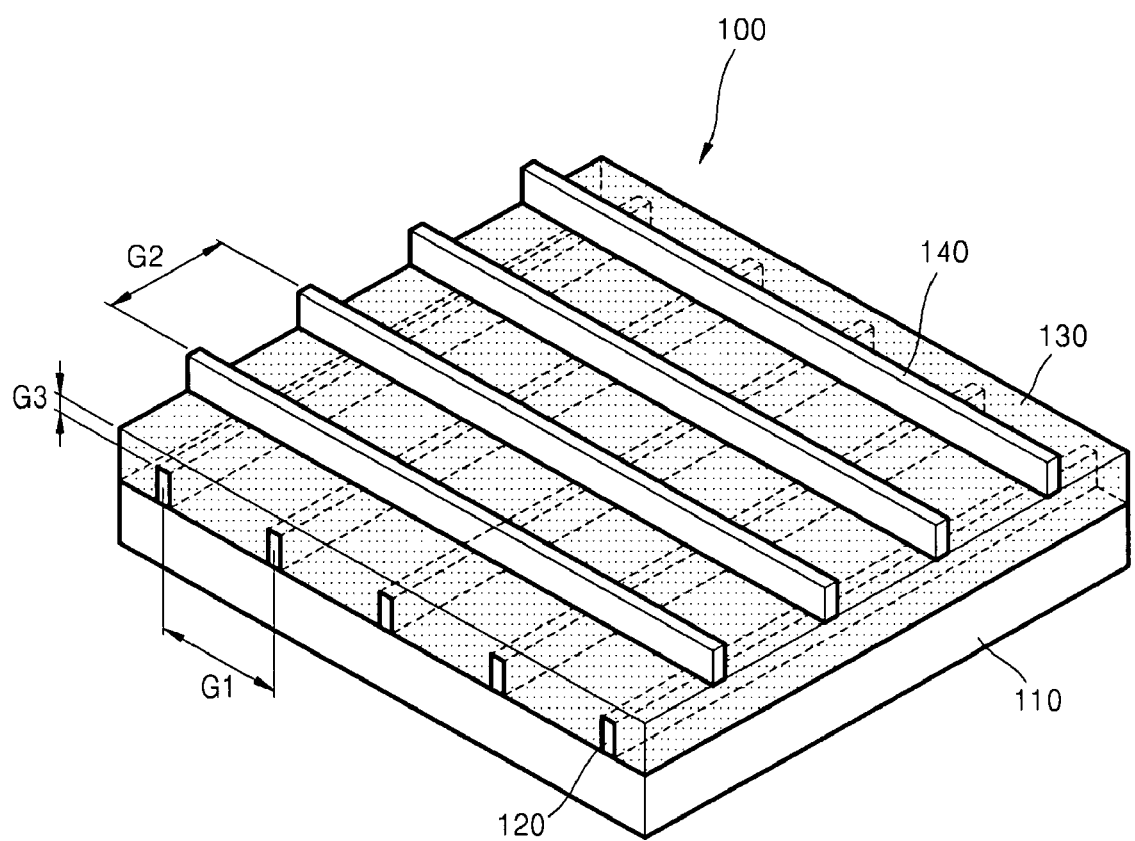
FIG. 1 is a schematic perspective view of the structure of a chemical sensor according to example embodiments.

Example embodiments will now be described more fully with reference to the accompanying drawings, in which example embodiments are shown. Example embodiments may, however, be embodied in different forms and should not be construed as limited to example embodiments set forth herein. Rather, example embodiments are provided so that this disclosure will be thorough and complete, and will fully convey the scope of example embodiments to those skilled in the art. In the drawings, the sizes of components may be exaggerated for clarity.

It will be understood that when an element or layer is referred to as being "on", "connected to", or "coupled to" another element or layer, it can be directly on, connected to, or coupled to the other element or layer or intervening elements or layers that may be present. In contrast, when an element is referred to as being "directly on", "directly connected to", or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. Thus, a first element, component, region, layer, or section discussed below could be termed a second element, component, region, layer, or section without departing from the teachings of example embodiments.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments described herein will refer to plan views and/or cross-sectional views by way of ideal schematic views. Accordingly, the views may be modified depending on manufacturing technologies and/or tolerances. Therefore, example embodiments are not limited to those shown in the views, but include modifications in configuration formed on the basis of manufacturing processes. Therefore, regions exemplified in figures have schematic properties and shapes of regions shown in figures exemplify specific shapes or regions of elements, and do not limit example embodiments.

Reference will now be made in detail to example embodiments illustrated in the accompanying drawings, wherein like reference numerals refer to the like elements throughout. In this regard, example embodiments may have different forms and should not be construed as being limited to the description set forth herein. Accordingly, example embodiments are merely described below, by referring to the figures, to explain aspects of the present description.

FIG. 1 is a schematic perspective view of a chemical sensor 100 according to example embodiments. Referring to FIG. 1, first nanowires 120 may be disposed parallel to each other on a substrate 110. Second nanowires 140 may be disposed parallel to one another above the first nanowires 120 so as to cross the first nanowires 120. As shown in FIG. 1, second nanowires 140 may be spaced apart from the first nanowires 120. A sensing member 130 may cover the first nanowires 120 and may be formed between the first nanowires 120 and the second nanowires 140.

The first nanowires 120 and the second nanowires 140 may each have a width of about 10 nm to about 10 μm and may be formed of a metal, for example, Al, Co, Au, or Pt. However, example embodiments are not limited thereto. For example, the first nanowires 120 and the second nanowires 140 may be formed of carbon nanotubes or patterned graphene.

A gap G1 between the first nanowires 120 and a gap G2 between the second nanowires 140 may be about 10 nm to about 10 μm. Also, the sensing member 130 may be formed to provide a gap G3 between the first nanowires 120 and the second nanowires 140 of about 10 nm to about 1 μm. The first nanowires 120 and the second nanowires 140 may be referred to as first electrodes and second electrodes.

The sensing member 130 may be formed of a metal oxide, a conductive polymer, or an insulating polymer. The metal oxide may be one of $SnO_2$, $TiO_2$, $ZnO$, $WO_3$, and $Fe_2O_3$. The conductive polymer and the insulating polymer may be impregnated with carbon nanotubes, graphene, or nanowires.

The conductive polymer may be formed of polyaniline, polypyrrole, polythiophene, Poly(ethylene-co-vinyl acetate), Poly(styrene-co-butadiene), Poly(9-vinylcarbazole), Poly(pyrrole)/1-butanesulfonate (BSA), or Poly(bithiophene)/tetrabutylammonium tetrafluoroborate (TBATFB). The insulating polymer may be impregnated with a conductive material, for example, carbon black, and accordingly, the conductivity of the insulating polymer may be controlled. BSA and TBATFB are added to their corresponding polymers. If an insulating polymer is used in the sensing member 130, the conductivity between the first nanowires 120 and the second nanowires 140 depends on a tunneling current.

Figure 2:
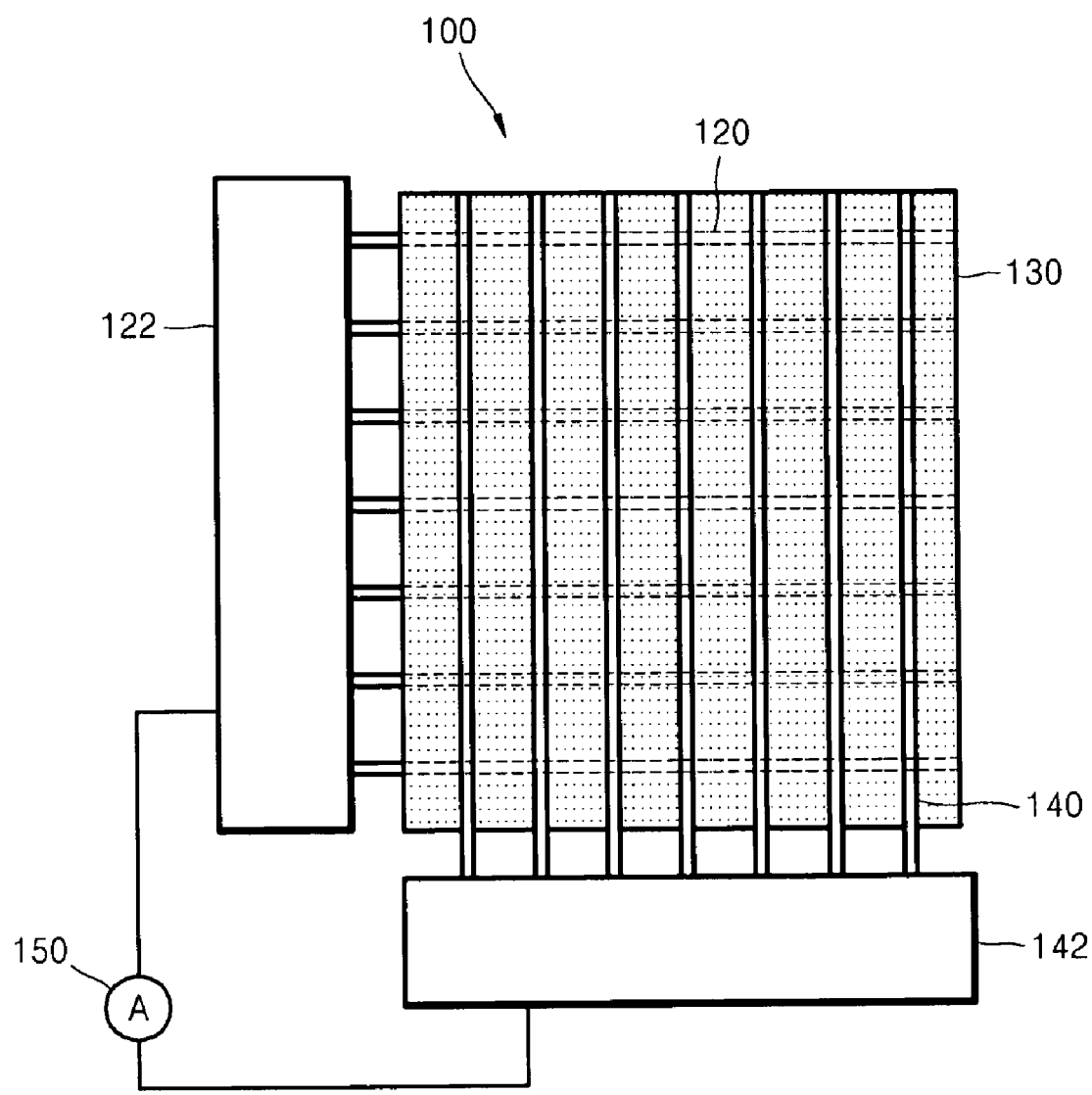
FIG. 2 is a plan view of the chemical sensor of FIG. 1, according to example embodiments.

FIG. 2 is a plan view of the chemical sensor 100 of FIG. 1, according to example embodiments, and for convenience, the substrate 110 is not shown. Referring to FIG. 2, the first nanowires 120 and the second nanowires 140 may be disposed perpendicular to each other. First ends of the first nanowires 120 may be connected to a first electrode pad 122 and first ends of the second nanowires 140 may be connected to a second electrode pad 142. The sensing member 130 may occupy a majority of an area of the chemical sensor 100, and thus, the sensitivity of the chemical sensor 100 may be increased. For convenience, the first electrode pad 122 and the second electrode pad 142 are not shown in FIG. 1. An ammeter 150 may be disposed between the first electrode pad 122 and the second electrode pad 142 to measure a current therebetween.

The operation principle of the chemical sensor 100, according to example embodiments, will now be described. When a compound is in contact with the chemical sensor 100, the compound may be adsorbed by the sensing member 130 of the chemical sensor 100. In the sensing member 130, contacts, for example, a nano contact array in which the first nanowires 120 and the second nanowires 140 cross each other, may be formed. The resistance of the sensing member 130 to which the compound is adsorbed may be changed, and the change of the resistance may be detected with a current difference. A read voltage is applied to the first electrode pad 122 and the second electrode pad 142, and the correct difference is measured from the ammeter 150. The read voltage may be in the range of several mV to 10V DC according to the sensing member 130 and the chemical sensor 100. When the current difference is detected, the concentration of the corresponding compound may be measured from the current difference.

In the chemical sensor 100, according to example embodiments, the nano contacts may be arranged in an array and in a nano size, and thus, although a compound having a concentration of a few ppm is adsorbed, the concentration of the compound may be measured. Also, the sensing member 130 may occupy a relatively large area of the chemical sensor 100, and thus, the sensitivity of the chemical sensor 100 may be increased.

Figure 3:
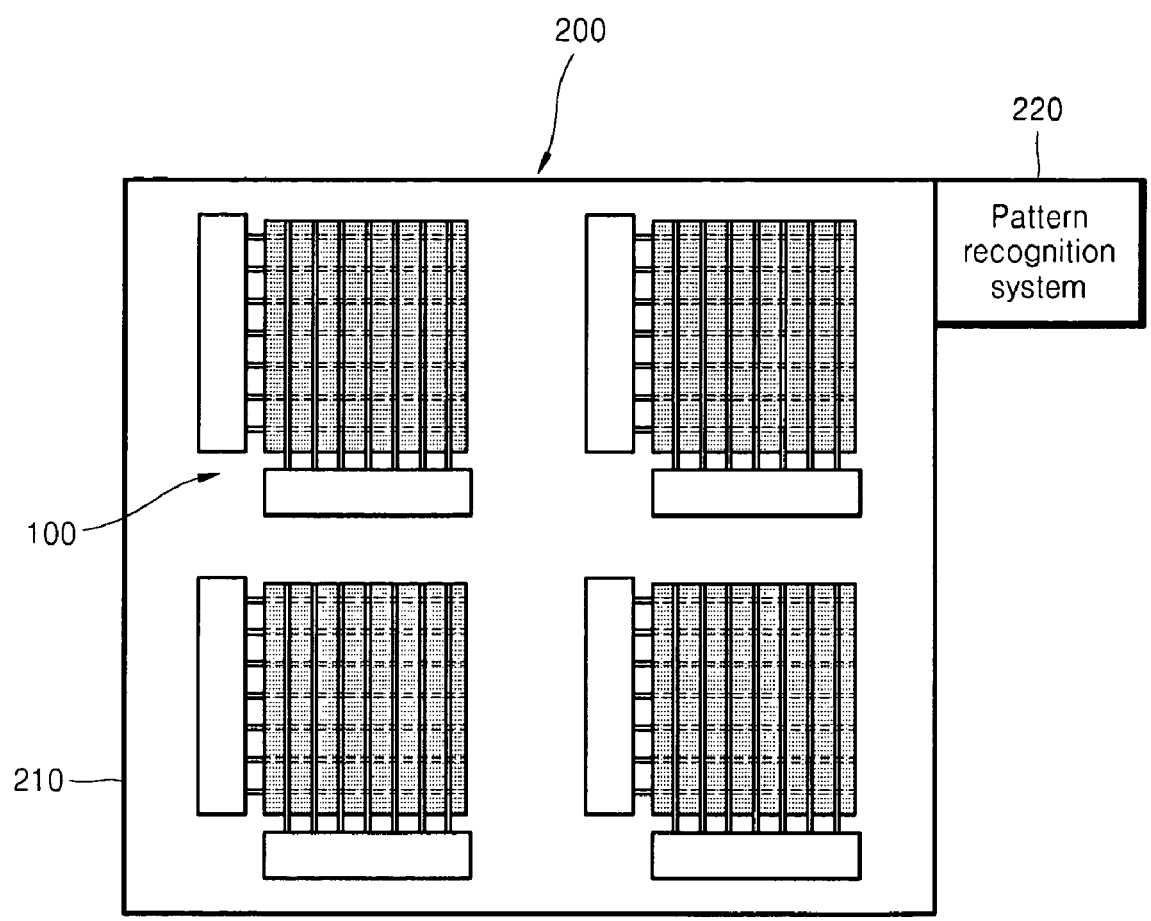
FIG. 3 is a schematic plan view of the arrangement of a chemical sensor array according to example embodiments.

FIG. 3 is a schematic plan view of the arrangement of a chemical sensor array 200 according to example embodiments. Like reference numerals are used to indicate elements substantially identical to the elements of the chemical sensor 100 of FIG. 1, and thus, the description thereof will not be repeated.

Referring to FIG. 3, a plurality of chemical sensors 100 may be disposed in an array on a substrate 210. First nanowires 120 of a chemical sensor 100 may be connected to a first electrode pad 122, and second nanowires 140 of the chemical sensor 100 may be connected to a second electrode pad 142. The first and second electrode pads 122 and 142 may be connected to a pattern recognition system 220.

When an analyte is absorbed on a sensing member 130, which is between the first and second nanowires 120 and 140, a work function between the first and second nanowires 120 and 140 may be changed. The change of the work function may be expressed in a resistivity or a conductivity difference.

The pattern analysis system 220 may measure the concentration of a compound in each of the chemical sensors 100.

The pattern analysis system 220 may analyze a current characteristic according to the adsorption concentration of the compound in each of the chemical sensors 100. The sensing member 130 of each of the chemical sensors 100 may have different configurations from each other. For example, if the work function of the sensing member 130 of each of the chemical sensors 100 is controlled by varying the kind and the gap between the first and second nanowires 120 and 140 of the sensing member 130, a chemical sensor having a correlation with the concentration of an adsorbed specific analyte may be manufactured.

As another example, different materials may be used for each of the sensing members 130. For example, the sensing member 130 of one chemical sensor 100 may be made from a metal oxide, for example, a metal oxide selected from the group consisting of $SnO_2$, $TiO_2$, ZnO, $WO_3$, and $Fe_2O_3$, and another sensing member 130 of another chemical sensor 100 may be made from a conductive polymer impregnated with carbon nanotubes. Therefore, each of the chemical sensors 100 may function as a chemical sensor for a specific compound, and the pattern analysis system 220 may measure the concentration of an adsorbed compound based on a characteristic curve prepared in advance.

Figure 4:
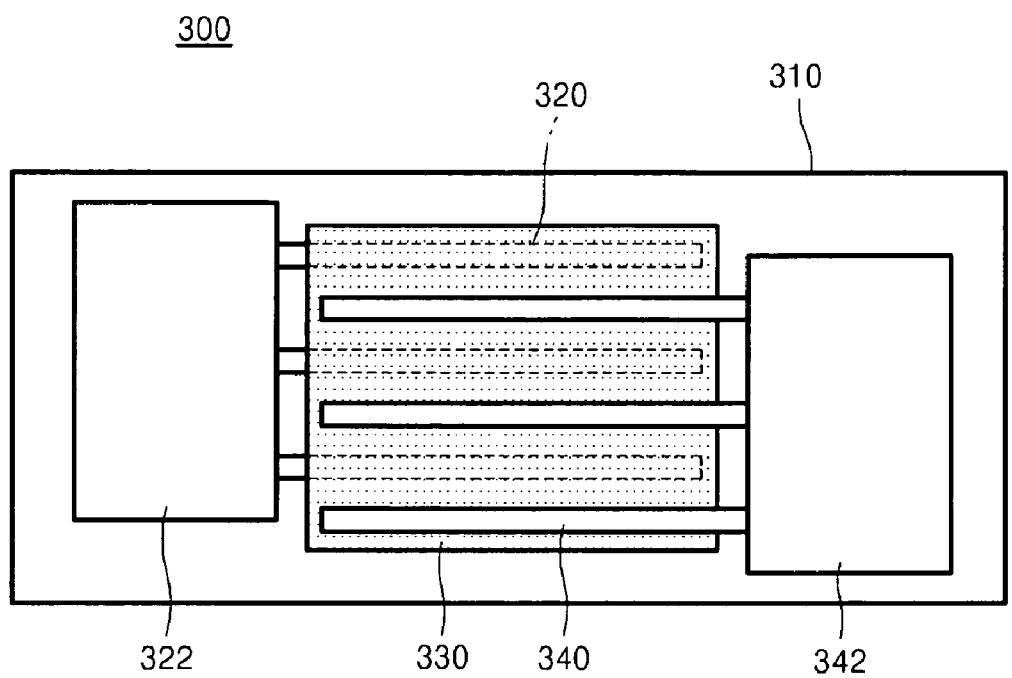
FIG. 4 is a schematic plan view of a chemical sensor according example embodiments.

FIG. 4 is a schematic plan view of a chemical sensor according to example embodiments. Referring to FIG. 4, a plurality of first nanowires 320 may be disposed parallel to each other on a substrate 310, and a sensing member 330 may be formed on the substrate 310 and may cover the first nanowires 320. A plurality of second nanowires 340 may be formed parallel to each other on the sensing member 330. The first nanowires 320 may be connected to a first electrode pad 322, the second nanowires 340 may be connected to a second electrode pad 342. The second nanowires 340 may be formed parallel to the first nanowires 320. In FIG. 4 and the second nanowires 340 and the first nanowires 320 may be alternately formed; however, example embodiments are not limited thereto. For example, the second nanowires 340 may be disposed directly above the first nanowires 320. The operation of the chemical sensor 300 of FIG. 4 is substantially the same as the operation of the chemical sensor 100 of FIG. 1, and thus, the description thereof will not be repeated.

Figure 5:
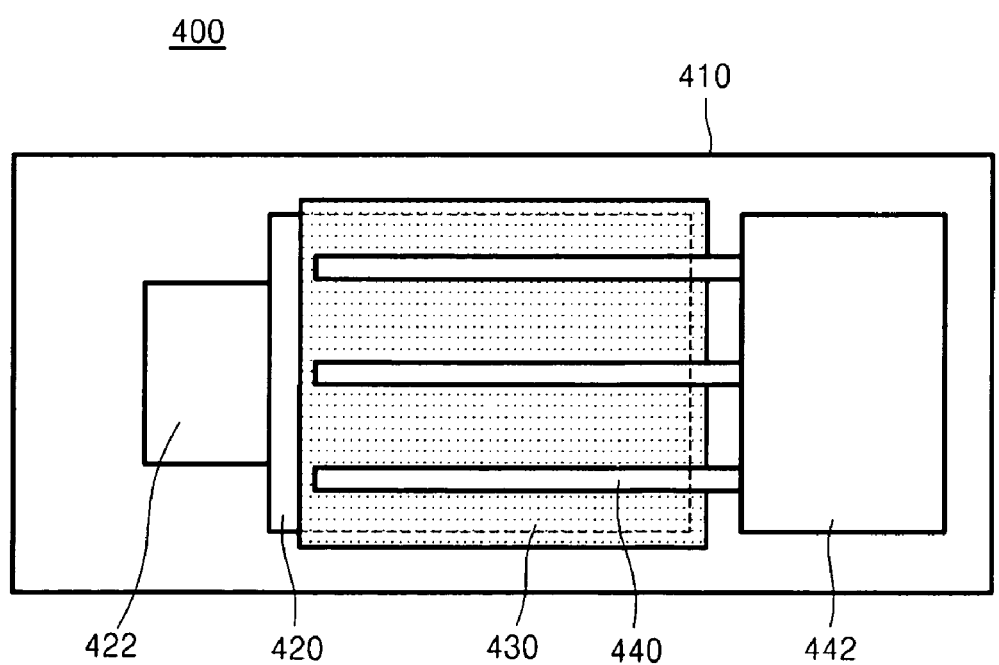
FIG. 5 is a schematic plan view of a chemical sensor according to example embodiments.

FIG. 5 is a schematic plan view of a chemical sensor 400 according to example embodiments. Referring to FIG. 5, a first electrode 420 having a flat panel shape may be formed on a substrate 410, and a sensing member 430 may be formed on the first electrode 420. Second electrodes 440 may be formed on the sensing member 430. Each second electrode 440 may be formed of a nanowire. A first electrode pad 422 may be connected to a first end of the first electrode 420, and a second electrode pad 442 may be connected to first ends of the second electrodes 440. The manufacture of the first electrode 420 may be relatively simple because the first electrode 420 may be a flat panel shape electrode, and the size of the first electrode pad 422 may be reduced as required. The rest of the configuration of the chemical sensor 400 may be substantially identical to the configuration of the chemical sensor 100 of FIG. 1, and thus, the description thereof will not be repeated.

Figure 6:
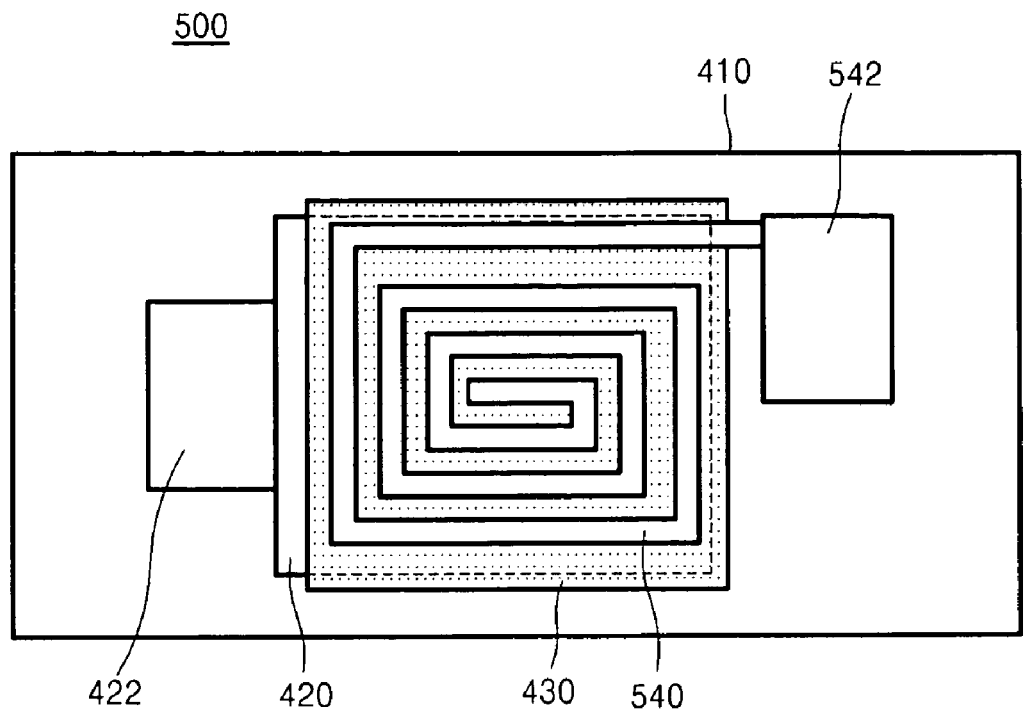
FIG. 6 is a schematic plan view of a chemical sensor according to example embodiments.

FIG. 6 is a schematic plan view of a chemical sensor 500, according to example embodiments. Referring to FIG. 6, a second electrode 540 may have a spiral shape. A second electrode pad 542 may be connected to the second electrode 540, thus the size of the second electrode pad 542 may be small compared to the second electrode pad 442 in FIG. 5. The rest of the configuration of the chemical sensor 500 is substantially identical to the configuration of the chemical sensor 400 of FIG. 5, and thus, the description thereof will not be repeated.

Figure 7A:
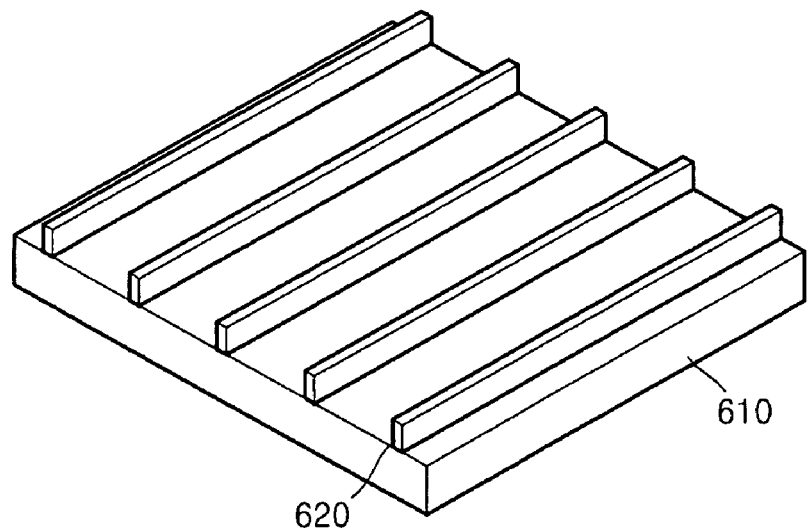
FIGS. 7A through 7C are perspective views for describing a method of manufacturing the chemical sensor of FIG. 1, according to example embodiments.
Figure 7B:
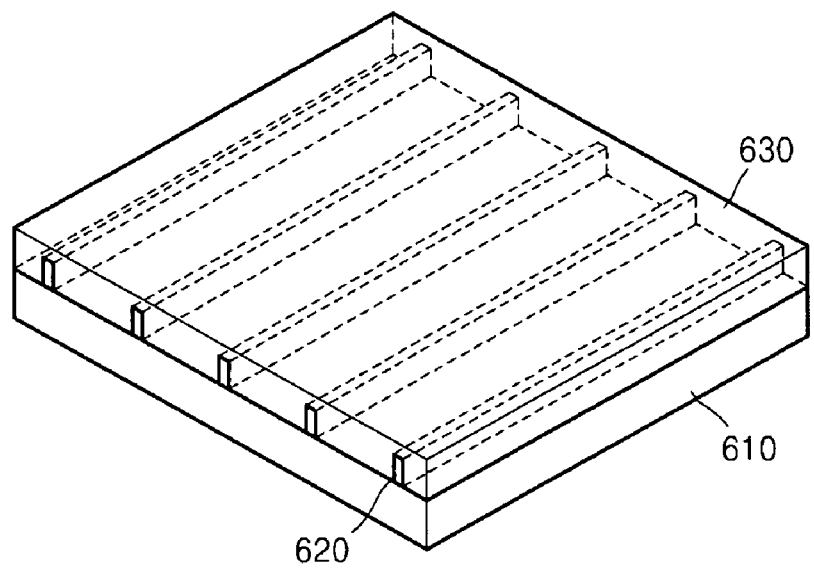
Figure 7C:
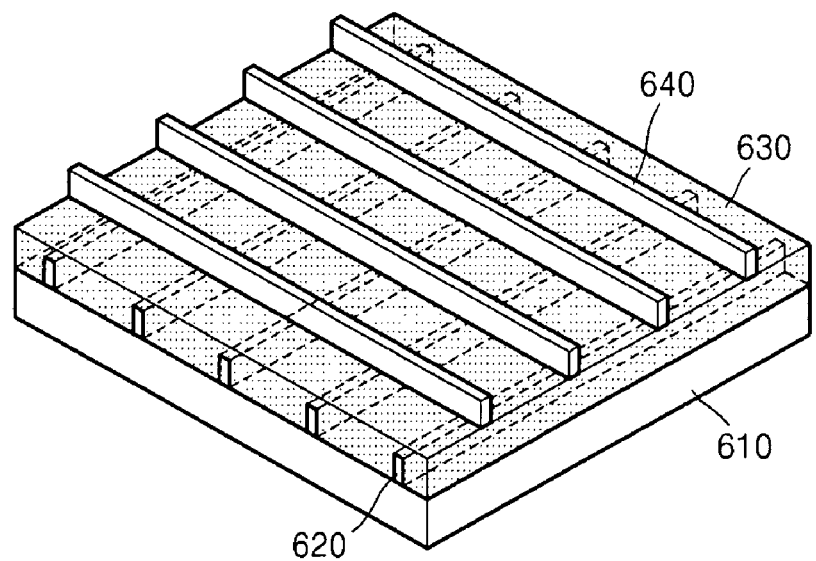

FIGS. 7A through 7C are perspective views for describing a method of manufacturing the chemical sensor of FIG. 1, according to example embodiments. Referring to FIG. 7A, a first metal layer (not shown), for example, Al, Co, Au, or Pt, may be deposited on a substrate 610. A plurality of first nanowires 620, which are parallel to each other, may be formed by patterning the first metal layer.

Referring to FIG. 7B, a conductive polymer layer 630, covering the first nanowires 620, may be formed on the substrate 610 using a spin coating method. The conductive polymer layer 630 may be formed to a few tens of nm higher than the first nanowires 620. For example, the conductive polymer layer 630 may be formed to be about 10 nm to about 1 µm higher than the first nanowires 620. To this end, a chemical-mechanical polishing (CMP) method may be used.

Referring to FIG. 7C, a second metal layer (not shown) may be deposited on the conductive polymer layer 630. The second metal layer may be formed using the same material used to form the first metal layer. Second nanowires 640 may be formed by patterning the second metal layer, such that the second nanowires 640 cross the first nanowires 620.

While example embodiments have been particularly shown and described with reference to example embodiments thereof, it will be understood by those of ordinary skill in the art that various changes in form and details may be made therein without departing from the spirit and scope of the following claims.

What is claimed is:

1. A chemical sensor comprising:
   a first electrode on a substrate;
   a sensing member covering the first electrode on the substrate; and
   a plurality of second electrodes on a surface of the sensing member exposing the surface of the sensing member,
   wherein the first electrode includes a plurality of nanowires.

2. The chemical sensor of claim 1, wherein each of the plurality of second electrodes has a width of about 10 nm to about 10 µm.

3. The chemical sensor of claim 1, wherein a gap between the first electrode and the plurality of second electrodes is about 10 nm to about 1 µm.

4. The chemical sensor of claim 1, wherein each of the second electrodes of the plurality of second electrodes includes a nanowire.

5. The chemical sensor of claim 4, wherein the plurality of second electrodes crosses the first electrode.

6. The chemical sensor of claim 4, wherein the first electrode and the plurality of second electrodes are parallel to each other.

7. The chemical sensor of claim 1, wherein the sensing member includes a material selected from the group consisting of a metal oxide, a conductive polymer, and an insulating polymer.

8. The chemical sensor of claim 7, wherein the metal oxide is one selected from the group consisting of $SnO_2$, $TiO_2$, ZnO, $WO_3$, and $Fe_2O_3$.

9. The chemical sensor of claim 7, wherein the polymer is impregnated with at least one of carbon nanotubes, graphene, and nanowires.

10. A chemical sensor array comprising:
    a plurality of the chemical sensors of claim 1 arranged in an array on the substrate, wherein sensing members of the chemical sensors are configured to detect compounds that are different from each other.

* * * * *